United States Patent [19]
Worst

[11] Patent Number: 5,192,319
[45] Date of Patent: Mar. 9, 1993

[54] INTRAOCULAR REFRACTIVE LENS

[76] Inventor: Jan G. F. Worst, Julianalaan 11, Haren, Netherlands

[21] Appl. No.: 703,271

[22] Filed: May 20, 1991

[51] Int. Cl.$^5$ ............................................. A61F 2/16
[52] U.S. Cl. ........................................................ 623/6
[58] Field of Search ........................................... 623/6

[56] References Cited

U.S. PATENT DOCUMENTS

| | | | |
|---|---|---|---|
| 2,834,023 | 5/1958 | Lieb | 623/6 |
| 4,215,440 | 8/1980 | Worst | 623/6 |
| 4,277,851 | 7/1981 | Choyce | 623/6 |

Primary Examiner—Randy C. Shay
Attorney, Agent, or Firm—Joseph Zallen

[57] ABSTRACT

An intraocular lens surgically positioned in the anterior chamber and to be used in addition to the natural lens to correct the refraction. The lens is fixated by iris stromal support, comprising an optical portion of inner concave and outer convex shape and a side support portion which has one or more pairs of pincerlike extensions for holding a portion of iris tissue. The design provides safe clearance away from the vital structures both anteriorly and posteriorly. This technique of stromal iris support permits full pupil motility. Lack of any postoperative decentration allows the system to be used for myopia, hyperopia, presbyopia or astigmatism. A non-transparent, light-impermeable ring may be incorporated to prevent glare or edge effects. The lens provides high predictability of the precalculated optical power.

10 Claims, 4 Drawing Sheets

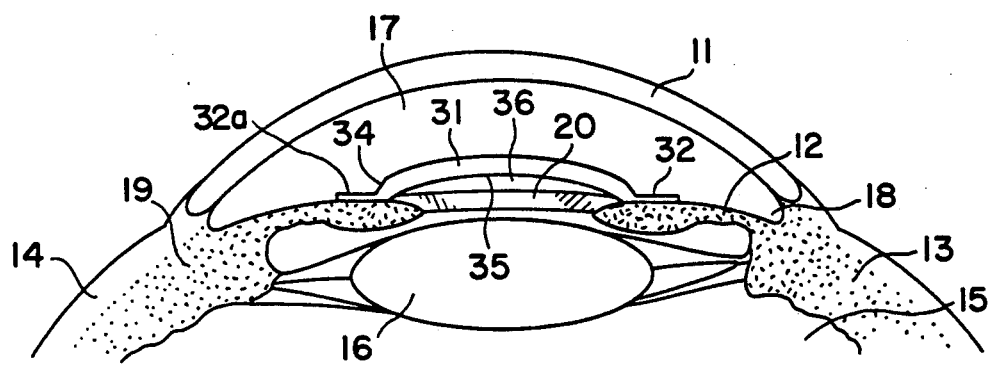
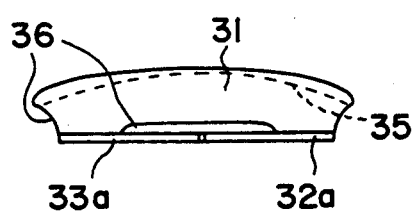
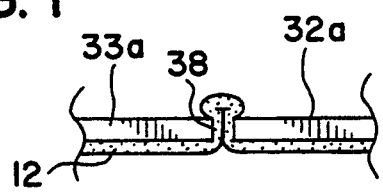
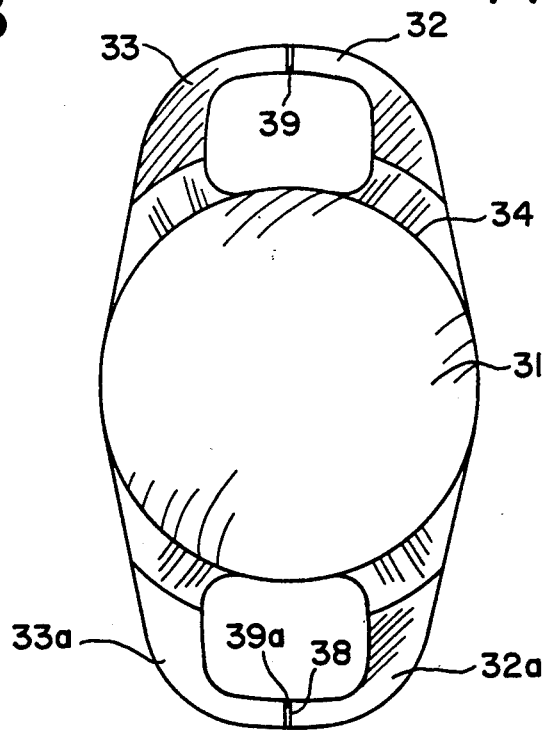

INTRAOCULAR REFRACTIVE LENS

BACKGROUND OF INVENTION

The present invention relates to surgical refractive correction wherein the result is a correction of the normal refraction of the eye to permit improved vision Surgical correction of corneal curvature has been proposed in various forms, such as correction with radial keratotomy, excimer laser, corneal inlays, epikeratophakia, or keratomileusis. In addition, surgical corrections have been disclosed, wherein the correction is achieved by an anterior chamber biconcave implant, in addition to the natural lens (phakic eye). In one example, a biconcave lens, manufactured by Domilens, France, is supported by the chamber angle, which can lead to serious complications such as corneal edema, chronic iridocyclitis or hyphema, generally known as being related to chamber angle supported anterior chamber implant The height of this lens and the biconcave optics add an additional risk of corneal edema and corneal decompensation. In another example, as described in "European Journal Ref. Surgery", Vol. 1, page 41-43, March 1989, a biconcave lens is supported by iris claws (U.S. Pat. No. 4,215,440 describes iris claws.). Although such biconcave lenses can provide a high predictability of precalculated refraction, the height of the lens and the biconcavity may be a risk of corneal edema or corneal decompensation in shallow anterior chambers Other examples of prior art implant lenses intended for refractive correction include U.S. Pat. No. 4,585,456 in which the optical body is positioned against the natural lens; U.S. Pat. No. 4,769,035 in which the optical body is also positioned against the natural lens, and U.S. Pat. No. 4,950,288 in which the lens is flat inside and supported by the chamber angle.

OBJECTS OF THE INVENTION

The principal object of the present invention is to provide a novel intraocular lens, the entire structure of which is located in the anterior chamber as an addition to the natural lens (phakic eye) and which is fixated by iris stromal support providing a system with a high predictability of the precalculated refraction for correction of myopia or hyperopia or presbyopia and astigmatism.

Other objects and advantages of this invention will be apparent from the description and claims which follow taken together with the appended drawings

SUMMARY OF THE INVENTION

The invention comprises broadly an intraocular lens having an optical portion whose inner curvature is concave and outer curvature convex with a specific geometrical shape. The shape is adapted to the anatomy and physiology of the cornea, the iris, the aqueous outflow through the pupillary area and the clearance between the natural lens and the optical portion of the intraocular lens in the case of implantation in a phakic eye.

The support portion of the intraocular lens, which comprises one or more pairs of flexible pincer arms, provides full pupil motility, a safe distance from chamber angle and trabecular meshwork and a safe distance from the corneal endothelium as a result of the impossibility of post operative decentration. The arms can be placed symmetrically or asymmetrically. The optical design guarantees safe clearance away from all vital structures anteriorly and posteriorly.

This invention relates particularly to an intraocular lens which is surgically implanted into the eye with the purpose of adding or subtracting the refractive power of the natural lens with the purpose of correcting myopia, hyperopia, presbyopia or astigmatism. It may also be used to provide lost power in the case of aphakia.

It is preferred that all embodiments of this invention be made of a clinical quality clear plastic material such as polymethylmethacrylate or polycarbonate, or any other materials with a combination of high flexibility ratios, resulting in proper pincer movement and a high refractive index, resulting in a lens with considerably thinner optics and a larger distance to the corneal endothelium.

SIGNIFICANT ADVANTAGES AND FEATURES OF THE INVENTION

The present invention pertains to an intraocular lens with pincerlike extensions for fixation to the iris, thus preventing postoperative decentration and moreover an intraocular lens with an inner concave and outer convex curvature providing safe clearance from critical posterior and anterior eye tissues. The lens may also have a non-transparent light-impermeable ring to prevent glare or edge effects. The intraocular lens is surgically implanted into the eye with the purpose of adding or subtracting the refractive power of the natural lens in the phakic eye in the case of correcting myopia, hyperopia, presbyopia or astigmatism thus providing an optical system with high predictability of the precalculated dioptric power. The intraocular lens can also be used to provide lost power in the aphakic eye.

The choice of which correction to use is a medical decision. However, they are all very different in what they accomplish. Spectacles provide a limited field and disturbed peripheral vision. A contact lens provides a better peripheral vision, but cannot always be well tolerated by the eye. Correction by radial keratotomy provides only limited dioptric power correction (4-6 dpt). Moreover the predictability of the optical correction is poor. Correction by excimer laser provides limited dioptric power correction (4-6 dpt). It requires a complicated and expensive apparatus. Long-term results are not known. Correction by corneal inlays provide dioptric power fluctuation in correction (Reduction of refractive correction with time) The predictability of the optical correction is poor. Correction by keratomileusis provides a result with poor predictability. The surgical technique is difficult and requires complicated and expensive instrumentation.

In the present invention, the intraocular lens for refractive surgery (myopia, hypermetropia, presbyopia and astigmatism correction) in the phakic eye, with convex-concave optics, guarantees safe clearance from vital structures like natural lens and corneal endothelium. Stromal iris support ensures full pupil motility and prevents decentration. The back curve combined with side gates provides natural outflow of aqueous through the pupillary area Incorporating a non-transparent, light-impermeable ring eliminates glare and edge effects.

None of the prior art techniques can be used for the principal purpose covered by the invention namely, safe, accurate predictable correction of myopia, hyperopia, presbyopia or astigmatism.

BRIEF DESCRIPTION OF DRAWINGS

FIG. 1 is a sectional view of one embodiment of this invention implanted in the eye.

FIG. 2 is a plan view of this embodiment.

FIG. 2A is an enlarged partial sectional view of FIG. 1.

FIG. 3 is an end view of this embodiment.

SPECIFIC EXAMPLE OF INVENTION

Figure 6:
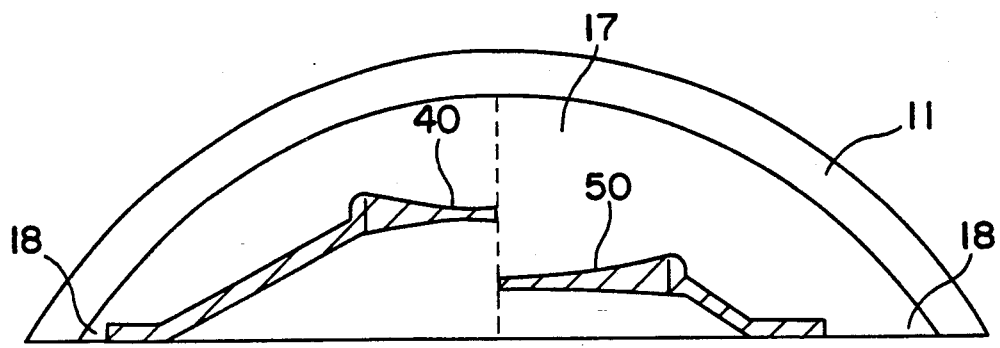
FIG. 6 is a cross-sectional diagrammatic view comparing an angle supported biconcave lens (mfg. by Domilens) on the left with an example of an iris stromal supported biconcave lens on the right. (Both prior art).

Referring now to FIGS. 1, 2, 2A, and 3, the portions of the eye illustrated therein are the cornea 11, iris 12, sclerotic tissue 14, vitreous 15, anterior chamber 17, chamber angle 18, and trabecular meshwork 19. The regular human lens is shown at 16. In the course of this invention the convex-concave optical portion 31 with its pairs of pincer arms 32, 33, 32a and 33a is fixed in the anterior chamber wherein the pairs of pincers grasp iris tissue 12 to form bulge 38, thus positioning the optical portion of the present invention directly in front of the natural lens 16. The arms 32, 33, are spaced apart with gap 39 therebetween. Gap 39a is between arms 32a and 33a. The inner surface of the optical portion 31 is concave, providing a safe distance to the natural lens. The outer surface is convex. The flexible pincerlike arms 32 permit full pupil motility and are a safe distance from the chamber angle 18, the trabecular meshwork 19, and the corneal endothelium 11. The tips of the pincerlike arms are covered by ,the iris tissue 12, which reduces the possibility of corneal dystrophy. The lens has four lateral side gates 36 to permit the aqueous to flow undisturbed from the pupillary area 20. Two of the side gates communicate with gaps 39 and 39a.

Figure 4:
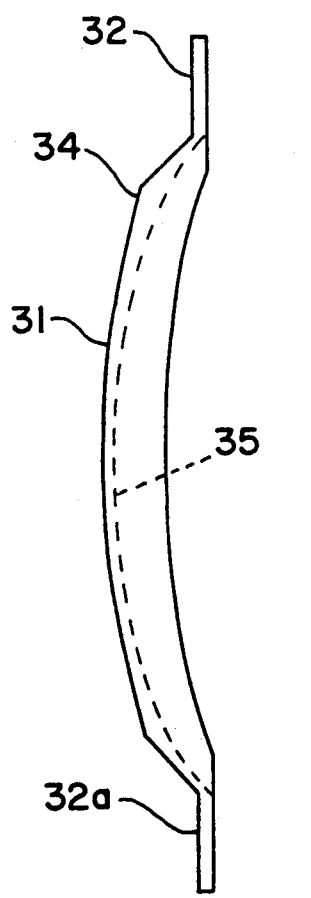
FIG. 4 is a side view of this embodiment.
Figure 5:
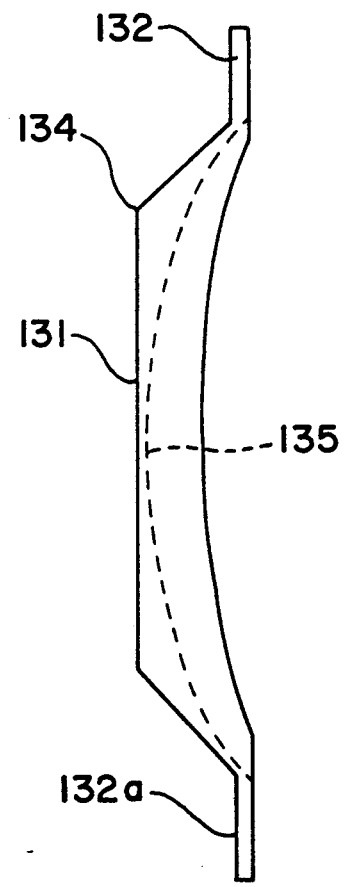
FIG. 5 is a side view of another embodiment of this invention with a plano outer surface.

FIGS. 4 and 5 show a comparison of a −10 diopter in FIG. 4 and a −25 diopter lens in FIG. 5. The outer portion of each ocllar has a peripheral highest point 34,, 134, a curved surface 31 or a flat surface 131 with iris clasping pairs of pincers 32, 32a, and 132, 132a. Because the tips of the pincerlike arms 32 are covered by the iris 12, even if there is an occasional touch to the cornea,. the touch would be by iris tissue and not by the lens materials, greatly reducing the possibility of corneal dystrophy. The post operative decentration and dislocation rate of the intraocular lens with pincerlike fixation is almost zero.

As illustrated in FIG. 6 a biconcave lens 40 of the prior art is shown fixated to the chamber angle 18 in the anterior chamber 17. On the right side is shown an example of a biconcave lens 50 of the prior art fixated to iris tissue by pincerlike arms.

Figure 7:
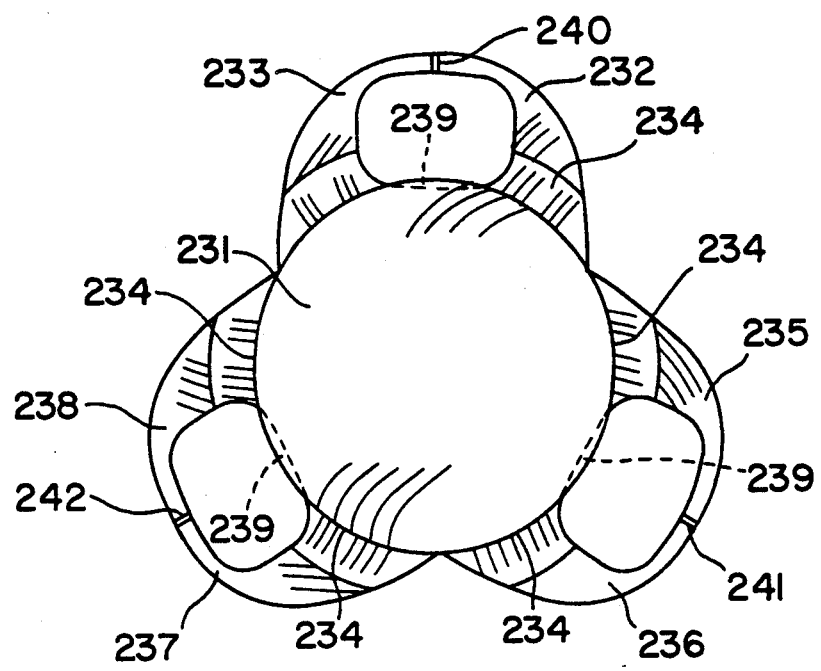
FIG. 7 is a plan view of another form of this invention: a lens supported by three pincer pairs.

As shown in FIG. 7, the support portion for optical portion 231 comprises three equally spaced pairs of pincer arms 232, 233; 237, 238; and 235, 236, with side gates 239 and peripheral highest points 234 and slits 240, 241, and 242.

Figure 8:
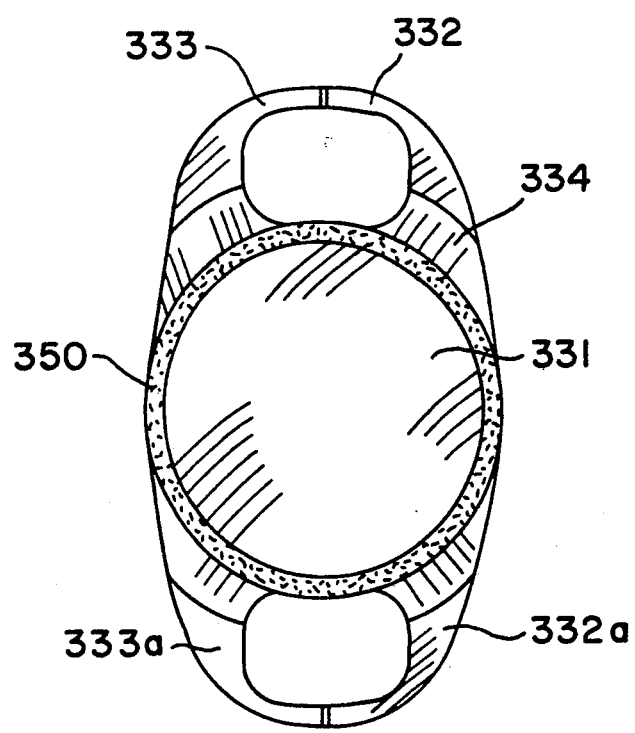
FIG. 8 is a plan view of another form of this invention: showing a peripheral, non-transparent ring embedded in the body of the optical portion.

In FIG. 8 the optical portion 331 has a peripheral non-transparent portion 350 to prevent glare, but otherwise has similar pairs of iris pincer arms 332, 333, 333a, and 332a and peripheral highest point 334.

Figure 9:
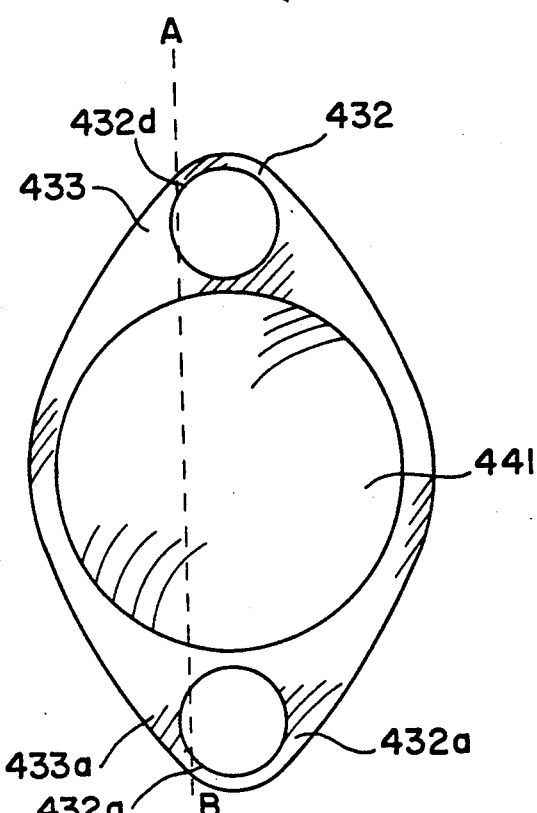
FIG. 9 is a plan view of another form of this invention: unequal length pincer arms and asymmetrically placed slits along fixation line a–b.

FIG. 9 illustrates an embodiment wherein the optical portion 441 has off- center pairs of pincer arms of unequal length 432, 433, and 432a, 433a, with asymmetrically placed abutting slits 432d and 432g along line A–B.

Figure 10:
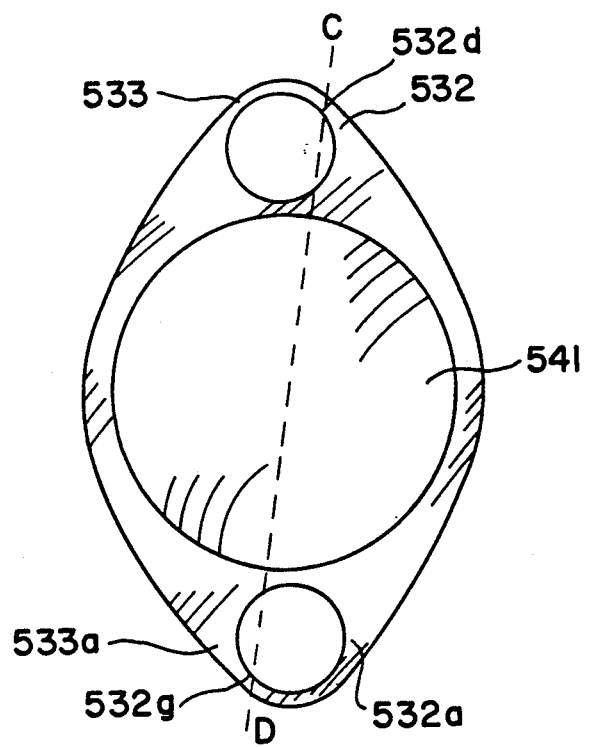
FIG. 10 is a plan view of another form of this invention: Unequal length pincer arms and mirror symmetrically placed slits along fixation line c–d

FIG. 10 illustrates an embodiment wherein the optical portion 541 has off-center pairs of pincer arms of unequal length 532, 533, and 532a, 533a with mirror symmetrically placed abutting slits 532d and 532g along line C–D.

Varieties of the invention can be made of other materials where a combination of high flexibility of lens material and a high refractive index, result respectively in a proper pincer movement and fixation performance and a lens with the largest critical distance to the corneal endothelium.

All designs are a compromise between the anatomical limitations caused by the position of the intraocular lens in the anterior chamber and the optical requirements.

Construction of equal length arms gives equal tensile strength and flexibility to each arm. Placing the slit asymmetrically provides a lens with unequal arms. One arm will obtain a greater mobility, facilitating in some situations the technical surgical procedure.

An anatomically correct convex-concave optical design is obtained with this invention where a negative power is obtained by combining a back curve of a fixed high dioptric power with a front curve of a lower power, resulting in a negative power lens to correct high myopia. Where the design has a back curve of a fixed dioptric power with a front curve of a higher power one can obtain a positive power lens to correct hyperopia or presbyopia. If the design has a back curve .of a fixed dioptric power with a front curve of a cylinder curve it can correct astigmatism.

I claim:

1. An iris tissue support fixation intraocular lens comprising:
   a) an optical portion having a periphery and adapted to be positioned in the anterior chamber of a phakic eye;
   b) a support portion extending radially from the optical portion, and comprising flexible, normally abutting pincer arm means for pinching a portion of the anterior surface only of iris tissue without penetrating to the posterior surface;
   c) said pincer arm means comprising a plurality of pincer arms that define generally a plane, and including at least first and second pairs of pincer arms that are spaced circumferentially about the optical portion;
   d) a gap positioned between the two pincer arms that form each of the pairs, said gaps communicating with the periphery of the optical portion;
   e) said optical portion being a lens having a flat or convex curve on its front and a concave curve on its back, said concave curve forming, when the pincer arms pinch the anterior surface of the iris tissue, a space between said optical portion and the pupil of the eye, said space being defined generally by said optical portion and said plane; and f) a plurality of lateral side gates formed in the optical portion and positioned between the optical portion and the gap between respective pairs of pincer arms, and each gate communicating with the space.

2. The intraocular lens of claim 1 wherein said support portion comprises two opposite pairs of said pincer arms.

3. The intraocular lens of claim 1 wherein said support portion comprises three pairs of said pincer arms.

4. The intraocular lens of claim 1 wherein said optical portion has a light-impervious portion on its periphery.

5. The intraocular lens of claim 1 wherein said pincer arms are of unequal length and asymmetrically positioned.

6. The lens of claim 1 wherein there are 2 additional lateral side gates, each positioned along the optical portion and spaced away from the gaps.

7. The lens of claim 1 wherein each of the pincer arms provides inner and outer end portions, each outer end portion abuts a corresponding outer end portion of an adjacent pincer arm, the outer end portions defining a grasping portion for grasping iris tissue.

8. The lens of claim 7 wherein the inner end portions attach to the lens at positions spaced circumferentially about the lens.

9. The lens of claim 1 wherein each of the pincer arms are arc shaped.

10. The lens of claim 1 wherein the optical portion is generally circular in shape.

* * * * *